United States Patent
Kimchy et al.

(10) Patent No.: US 9,826,945 B2
(45) Date of Patent: *Nov. 28, 2017

(54) FAIL SAFE RADIATION CONCEALMENT MECHANISM

(75) Inventors: Yoav Kimchy, Haifa (IL); Rafi Sommer, Nesher (IL)

(73) Assignee: CHECK-CAP LTD., Isfiya (IL)

( * ) Notice: Subject to any disclaimer, the term of this patent is extended or adjusted under 35 U.S.C. 154(b) by 392 days.

This patent is subject to a terminal disclaimer.

(21) Appl. No.: 13/821,999

(22) PCT Filed: Jun. 9, 2011

(86) PCT No.: PCT/IL2011/000462
§ 371 (c)(1),
(2), (4) Date: Mar. 11, 2013

(87) PCT Pub. No.: WO2012/035528
PCT Pub. Date: Mar. 22, 2012

(65) Prior Publication Data
US 2013/0172740 A1  Jul. 4, 2013

Related U.S. Application Data

(60) Provisional application No. 61/344,693, filed on Sep. 15, 2010.

(51) Int. Cl.
*A61B 6/00* (2006.01)
*A61B 5/00* (2006.01)
(Continued)

(52) U.S. Cl.
CPC ........ *A61B 6/4057* (2013.01); *A61B 1/00027* (2013.01); *A61B 1/041* (2013.01);
(Continued)

(58) Field of Classification Search
None
See application file for complete search history.

(56) References Cited

U.S. PATENT DOCUMENTS 4,262,271 A * 4/1981 Bowers et al. ............... 335/263
4,788,463 A * 11/1988 Layh ....................... F16D 51/00
188/161

(Continued)

FOREIGN PATENT DOCUMENTS

IL  WO 2008096358 A2 * 8/2008 ........... A61B 6/4057
WO  WO 2000/096358  8/2008

OTHER PUBLICATIONS

"Eddy Current," Aug. 25, 2009, Wikipedia, <https://en.wikipedia.org/wiki/Eddy_current>.*

(Continued)

Primary Examiner — Tse Chen
Assistant Examiner — Nate S Sunwoo
(74) Attorney, Agent, or Firm — Soroker Agmon Nordman

(57) ABSTRACT

An aspect of an embodiment of the invention, relates to an imaging capsule for scanning inside a living body with a fail-safe radiation mechanism that prevents the emission of radiation from the imaging capsule until the imaging capsule is instructed to emit radiation and power is available to activate a motor to unblock the emission of radiation. Optionally, when power is not available the imaging capsule automatically, blocks the emission of radiation.

19 Claims, 5 Drawing Sheets

(51) Int. Cl.
  *A61B 1/00* (2006.01)
  *A61B 1/04* (2006.01)
  *A61B 6/06* (2006.01)
(52) U.S. Cl.
  CPC .............. *A61B 5/6861* (2013.01); *A61B 6/06* (2013.01); *A61B 6/425* (2013.01); *A61B 6/548* (2013.01); *A61B 2562/162* (2013.01)

(56) References Cited

U.S. PATENT DOCUMENTS

| | | | | |
|---|---|---|---|---|
| 6,246,057 | B1* | 6/2001 | Nguyen | G01T 1/1648 250/363.04 |
| 6,442,799 | B1* | 9/2002 | Duarte et al. | 16/277 |
| 8,068,897 | B1* | 11/2011 | Gazdzinski | 600/476 |
| 2001/0051766 | A1 | 12/2001 | Gazdzinski | |
| 2011/0152639 | A1* | 6/2011 | Matott | 600/302 |
| 2013/0018491 | A1* | 1/2013 | Kelly | G01N 1/2035 700/90 |

OTHER PUBLICATIONS

"Eddy-current braking: a long road to success," Jun. 2, 2008, Railway Gazette, http://www.railwaygazette.com/news/single-view/view/eddy-current-braking-a-long-road-to-success.html, pp. 1-3.*

* cited by examiner

FAIL SAFE RADIATION CONCEALMENT MECHANISM

RELATED APPLICATIONS

The present application claims priority from U.S. Provisional application No. 61/344,693 filed on Sep. 15, 2010, the disclosure of which is incorporated herein by reference.

FIELD OF THE INVENTION

The present invention relates generally to limiting exposure of a patient to radiation and more specifically to a fail safe radiation concealment mechanism in an imaging capsule that is swallowed by a patient to examine the patient's gastrointestinal tract.

BACKGROUND OF THE INVENTION

One method for examining the gastrointestinal tract for the existence of polyps and other clinically relevant features that may indicate regarding the potential of cancer is performed by swallowing an imaging capsule that will travel through the tract and view the patient's situation. In a typical case the trip can take between 24-48 hours after, which the imaging capsule exits in the patient's feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits Xrays or Gamma rays. The radiation is typically collimated to allow it to be controllably directed toward a specific area during the imaging process. In an exemplary case the imaging capsule is designed to measure Compton back-scattering and transmits the measurements (e.g. count rate) to an external analysis device, for example a computer or other dedicated instruments.

In a typical implementation a radio-opaque contrast agent is used so that a position with a polyp will have less contrast agent and will measure a larger back-scattering count. Alternatively, other methods may be used to image the gastrointestinal tract.

U.S. Pat. No. 7,787,926 to Kimchy the disclosure of which is incorporated herein by reference, describes details related to the manufacture and use of such an imaging capsule.

Use of an imaging capsule exposes the user to radiation, which may be potentially harmful. Accordingly, it is of interest to limit the user's exposure to radiation when not necessary, for example while the imaging capsule is located in positions that do not need to be measured. Typically, the imaging capsule may be designed with shutters that can be instructed to block the exit of radiation when not needed. However, there still exists the hazard that in case of malfunction of the imaging capsule, for example in case of a power failure radiation may be emitted without constraint.

It is thus desirable to design a fail safe radiation blocking mechanism that automatically blocks the emission of radiation and only allows radiation to be emitted if power is available and the device provides an instruction to allow radiation to be emitted.

SUMMARY OF THE INVENTION

An aspect of an embodiment of the invention, relates to an imaging capsule for scanning inside a living body, with a fail-safe radiation mechanism that prevents the emission of radiation from the imaging capsule until the imaging capsule is instructed to emit radiation and power is available to activate a motor to unblock the emission of radiation. Optionally, when power is not available the imaging capsule automatically, blocks the emission of radiation.

In an exemplary embodiment of the invention, a rotatable disk with a collimated radiation source is attached to a motor by its rotation axis. The disk is configured to rotate 360° and emit radiation from the collimated radiation source on the disk. An outer ring which also rotates around the same rotation axis as the rotatable disk surrounds the circumference of the rotatable disk. The outer ring includes areas which block radiation and areas which don't block radiation.

In an initial rest position the outer ring is situated relative to the rotatable disk such that the radiation emitted through the collimators is blocked. In an exemplary embodiment of the invention, responsive to commands from the imaging capsule the motor rotates the rotatable disk to a position that allows radiation to be emitted. Optionally, the rotatable disk continues to rotate in the same direction and drags the outer ring along while the outlets of the collimators are unblocked, so that the entire circumference of the imaging capsule is scanned for as many rotations as desired.

In an exemplary embodiment of the invention, the rotatable disk and outer ring are connected together with a spring so that the emission of radiation from the collimators will be blocked automatically when the motor stops turning the rotatable disk.

There is thus provided according to an exemplary embodiment of the invention, an imaging capsule for scanning inside a living body with a fail-safe radiation mechanism, including:

a radiation source;

a rotatable disk with the radiation source mounted on the disk and wherein the rotatable disk has a collimator structure allowing the emission of radiation from the radiation source substantially only from a few locations on the circumference of the disk;

an outer ring surrounding the circumference of the disk and configured to rotate relative to the disk; wherein the outer ring includes areas that block radiation and areas that are transparent to the emission of radiation; and wherein in a rest position the outer ring is situated relative to the rotatable disk such that the areas that block radiation are blocking the emission of radiation from the few locations on the circumference of the disk that allow the emission of radiation;

a motor for rotating the rotatable disk relative to the outer ring; and wherein the rotatable disk and outer ring are initially in the rest position blocking the emission of radiation until the motor is activated to rotate the rotatable disk and allow the emission of radiation.

In an exemplary embodiment of the invention, the imaging capsule further includes a spring coupling the rotatable disk to the outer ring, and wherein the spring is configured to automatically return the rotatable disk and outer ring to the rest position when the motor is deactivated. Optionally, the imaging capsule further includes flaps extending from the outer ring and an encasement with an inner lining enclosing the imaging capsule, wherein the flaps are in contact with the inner lining of the encasement and are held by a force that prevents the outer ring from rotating responsive to the torque of the spring and the rotation of the rotatable disk. In an exemplary embodiment of the invention, the force between the flaps and the inner lining is a friction force. Alternatively, the force between the flaps and the inner lining is an electromagnetic force. In an exemplary embodiment of the invention, the force between the flaps and the inner lining is controllable. Optionally, if the motor is deactivated and the force between the flaps and the inner lining is turned off, the outer ring will rotate to return the rotatable disk and outer ring to the rest position. In an exemplary embodiment of the invention, if the motor is deactivated and the force between the flaps and the inner lining is turned on, the rotatable disk will rotate to return the rotatable disk and outer ring to the rest position.

In an exemplary embodiment of the invention, the motor is connected to the rotatable disk with a clutch that allows the motor to rotate the rotatable disk in a specific direction and the rotatable disk can rotate back freely when the motor is deactivated. Optionally, the imaging capsule further includes an encasement with an inner lining enclosing the imaging capsule, wherein the inner lining applies an electromagnetic force on the outer ring, and wherein the electromagnetic force controllably prevents the outer ring from rotating responsive to the torque of the spring and the rotation of the rotatable disk. In an exemplary embodiment of the invention, the imaging capsule, further includes a first limiter attached to the rotatable disk and a second limiter attached to the outer ring, wherein the limiters prevent the rotatable disk and outer ring from leaving the rest position under the influence of the spring and the limiters force the outer ring to rotate with the rotatable disk under the force of the motor. Optionally, the rotatable disk and the outer ring are configured to controllably emit radiation 360 degrees around the rotatable disk. In an exemplary embodiment of the invention, the rotatable disk and the outer ring are configured to controllably emit radiation for a pre-selected amount of time or a pre-selected number of rotations. Optionally, the imaging capsule further includes a transceiver to receive instructions to activate or deactivate the motor. In an exemplary embodiment of the invention, the imaging capsule is pre-programmed to activate or deactivate the motor at specific times.

There is further provided according to an exemplary embodiment of the invention, a method of providing failsafe radiation while scanning inside a living body, including:

mounting a radiation source on a rotatable disk;

positioning collimators on the disk so that the radiation is substantially allowed to be emitted only from a few locations on the circumference of the disk;

placing an outer ring to surround the circumference of the disk and configured to rotate relative to the disk; wherein the outer ring includes areas that block radiation and areas that are transparent to the emission of radiation;

situating the outer ring and rotatable disk initially in a rest position wherein the outer ring is situated relative to the rotatable disk such that the areas that block radiation are blocking the emission of radiation from the few locations on the circumference of the disk that allow the emission of radiation;

receiving instructions to begin emitting radiation;

activating the motor to rotate the rotatable disk relative to the outer ring to a position that allows the emission of radiation.

In an exemplary embodiment of the invention, the method further includes connecting between the rotatable disk and outer ring with a spring so that they will return to the rest position automatically when the motor is deactivated.

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
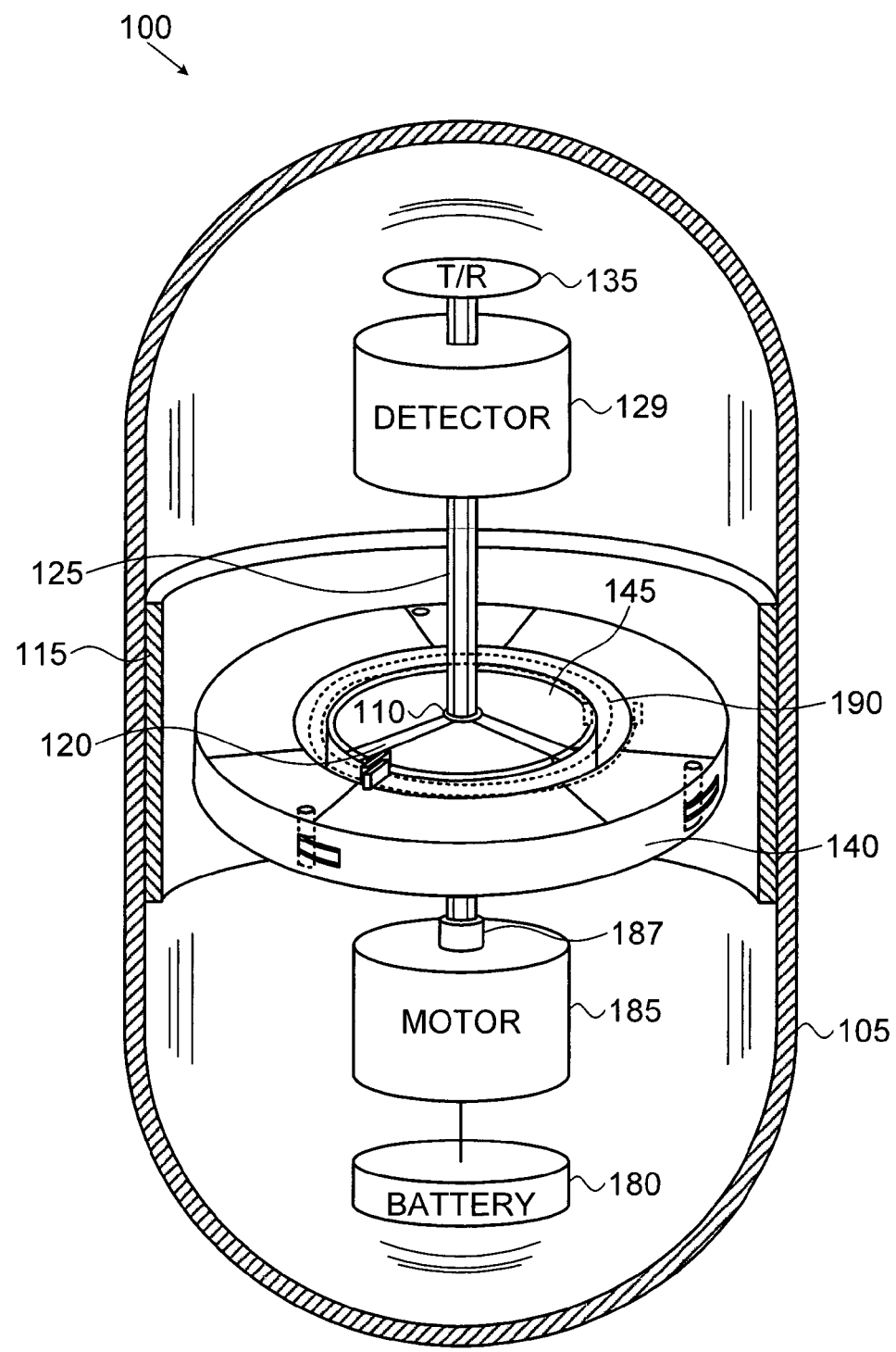
FIG. 1 is a schematic illustration of a perspective view of a failsafe imaging capsule, according to an exemplary embodiment of the invention.

FIG. 1 is a schematic illustration of a perspective view of a failsafe imaging capsule 100, according to an exemplary embodiment of the invention. In an exemplary embodiment of the invention, a patient first swallows a contrast agent which mixes with the content of their gastrointestinal tract to increase the accuracy of the measurements. Then the patient swallows imaging capsule 100 to examine the gastrointestinal tract as imaging capsule 100 proceeds through the gastrointestinal tract. In an exemplary embodiment of the invention, imaging capsule 100 is designed to automatically block radiation from being emitted from it until receiving instructions to release radiation and image its surroundings. In an exemplary embodiment of the invention, power is required to prevent blocking emission of radiation. Optionally, if imaging capsule 100 lacks power the radiation will be blocked.

In an exemplary embodiment of the invention, imaging capsule 100 includes an encasement 105 for holding and protecting the elements of the device from acids and other liquids or gases along its path of motion. Optionally, the encasement should be able to withstand external pressures for at least 50-100 hours to allow for imaging capsule 100 to traverse the gastrointestinal tract and exit while still intact. Inside encasement 105 imaging device 100 includes a power source 180 (e.g. one or more batteries), a motor 185, a radiation source 110, a detector 195 and a transceiver 135. In an exemplary embodiment of the invention, radiation source 110 is located on a rotatable disk 145 and provides radiation that is blocked by a filling material 130 that forms the disk (e.g. made of lead or tungsten or other dense materials). Optionally, the radiation is only free to travel in a few specific directions through collimators 120.

In an exemplary embodiment of the invention, power source 180 provides power to motor 185, motor 185 is configured to rotate disk 145 around a rotation axis 125 with radiation source 110 and collimators 120 mounted on disk 145. Optionally, one or more directed radiation beams are emitted from collimators 120 controllably scanning the surroundings through imaging capsule 100. Optionally, detector 195 detects backscattered particles resulting from the directed radiation beam. In an exemplary embodiment of the invention, detector 195 counts the detected particles and provides the information to transceiver 135 for transmission to an external device (e.g. a computer) for processing and optionally constructing a visual representation of the information. In some embodiments of the invention, transceiver 135 uses radio frequency (RF) transmissions to receive instructions from an external device and to provide information to the external device. Optionally, the external device may instruct imaging capsule 100 to start scanning, to stop scanning, to scan in a specific motion pattern or at specific times.

Figure 2:
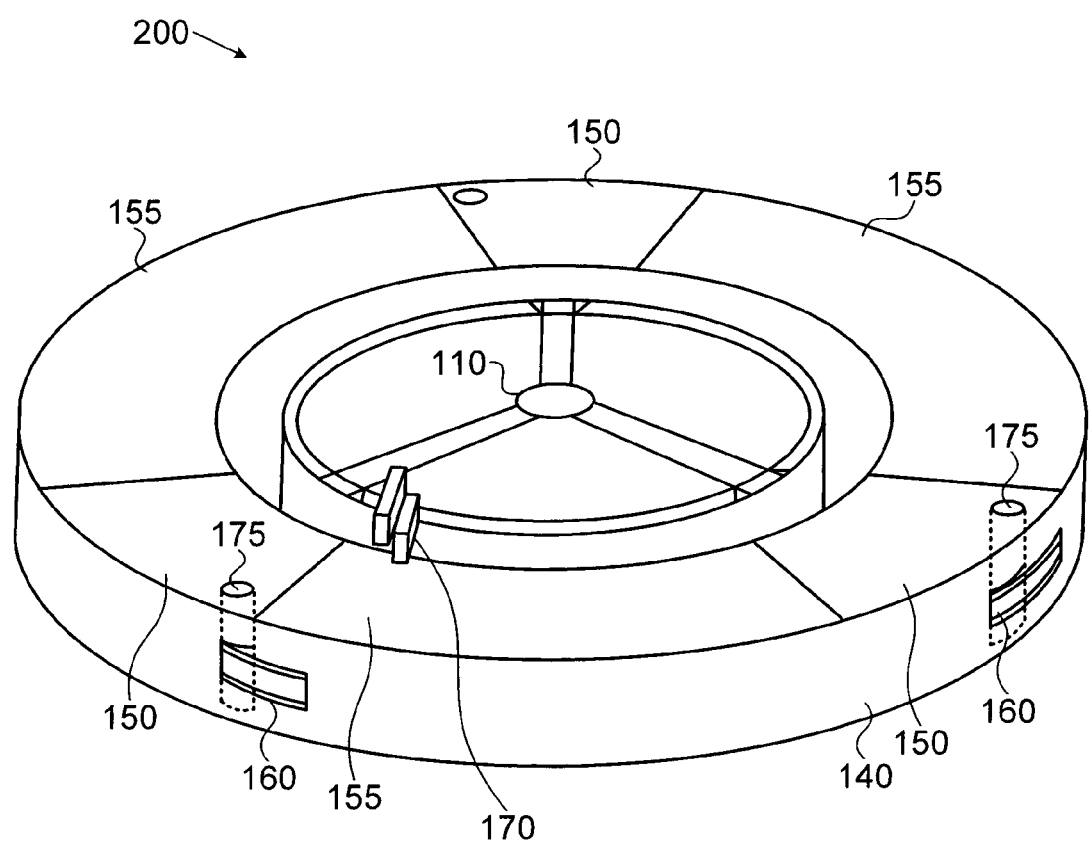
FIG. 2 is a schematic illustration of a perspective view of a radiation control mechanism, according to an exemplary embodiment of the invention.
Figure 3:
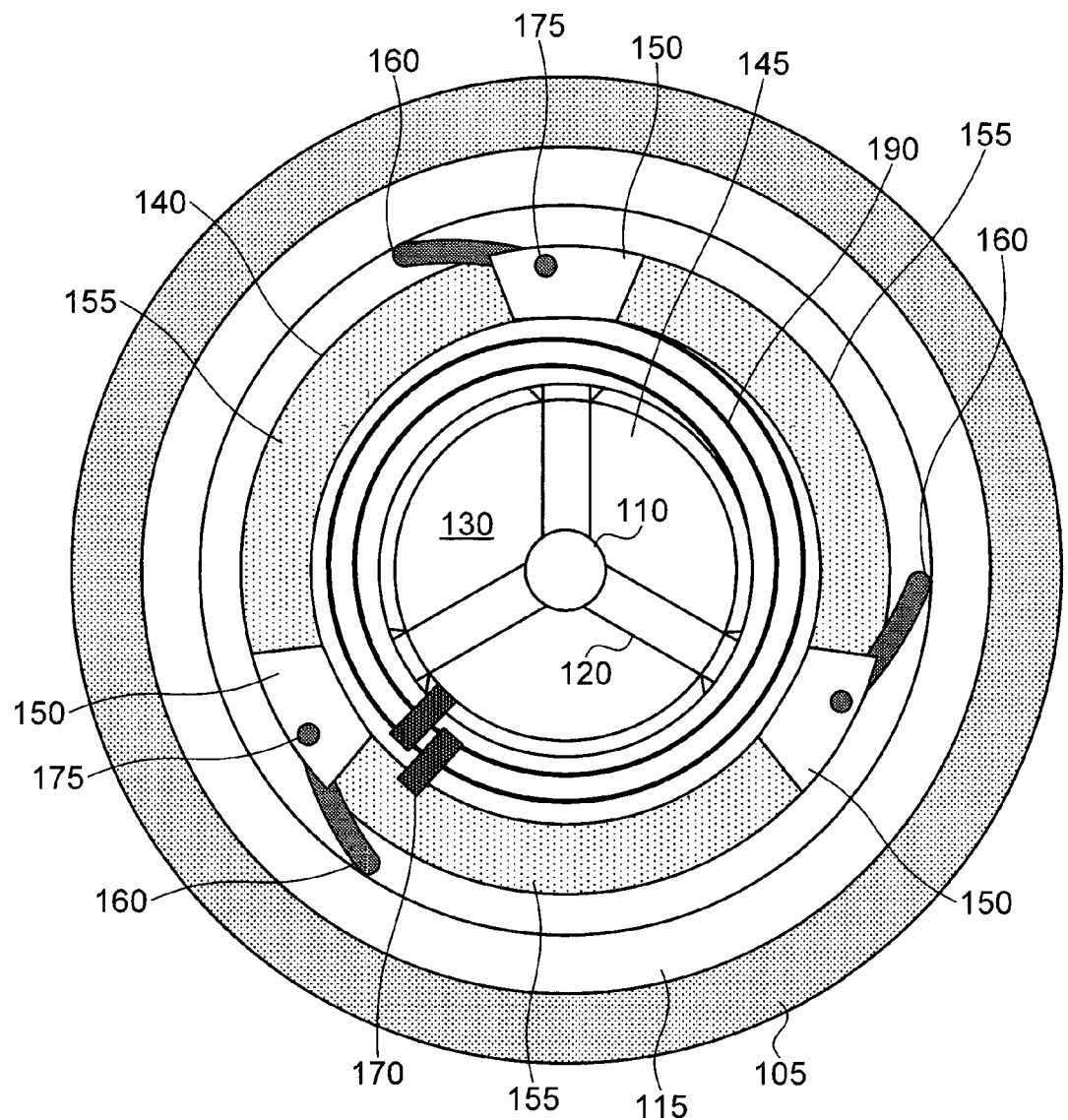
FIG. 3 is a schematic illustration of a top view of a radiation control mechanism, according to an exemplary embodiment of the invention.

FIG. 2 is a schematic illustration of a perspective view of a radiation control mechanism 200, and FIG. 3 is a schematic illustration of a top view of radiation control mechanism 200, according to an exemplary embodiment of the invention. In an exemplary embodiment of the invention, radiation control mechanism 200 includes disk 145 and an outer ring 140 that shares the same rotation axis 125 as disk 145 and is free to rotate surrounding the circumference of disk 145, for example by being connected to axis 125 from below disk 145. Optionally, outer ring 140 includes shutters 150, which are made up from a material that blocks radiation and the rest of outer ring 140 (transparent area 155) does not block radiation. In an initial rest position outer ring 140 is positioned so that shutters 150 coincide with the outlets of collimators 120, so that the emission of radiation from the collimators 120 is blocked.

In an exemplary embodiment of the invention, disk 145 and outer ring 140 are connected together with a spring 190, for example in the shape of a spiral. Optionally, if disk 145 is rotated (e.g. clockwise) the spring will tighten and exert a force on outer ring 140, so that it will aspire to follow suit. In an exemplary embodiment of the invention, outer ring 140 includes flaps 160 that extend from the sides of outer ring 140. Optionally, outer ring 140 includes a hinge 175, for example with an internal spring causing flaps 160 to extend outward from the side of outer ring 140 and causing them to be placed in contact with encasement 105 or a friction lining 115. In an exemplary embodiment of the invention, the friction between the flaps 160 and the friction lining 115 prevent outer ring 140 from initially rotating while disk 145 is rotating and the spring 190 is getting tighter.

Figure 4:
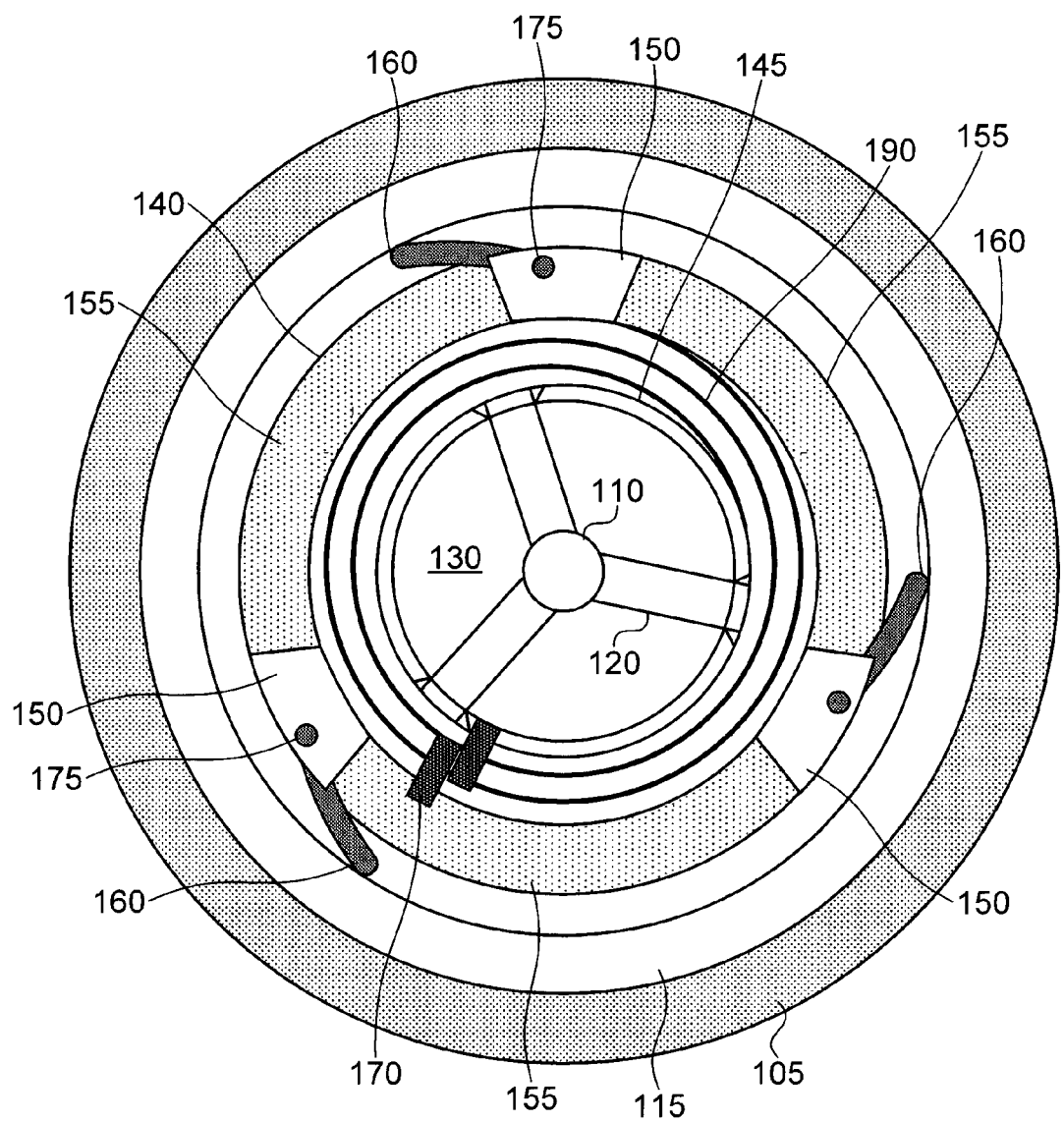
FIG. 4 is a schematic illustration of a top view of a radiation control mechanism in a rotated position, according to an exemplary embodiment of the invention.

FIG. 4 is a schematic illustration of a top view of radiation control mechanism 200 in a rotated position, according to an exemplary embodiment of the invention. As disk 145 rotates relative to outer ring 140, in some positions, shutters 150 stop blocking the outlets of collimators 120 and the radiation is freely emitted to scan the patient.

In some embodiments of the invention, a motion limiter 170 is attached to disk 170 and another motion limiter 170 is attached to outer ring 140. Optionally, in the rest position of radiation control mechanism 200, spring 190 is unwound, collimators 120 are blocked and the limiters prevent disk 145 from slipping and accidentally uncovering the outlets of collimators 120. Optionally, after rotating 360° as shown in FIG. 4 the collimators are open, and spring 190 is in a tightened position. Then motion limiters 170 meet on their opposite sides and the rotation of disk 145 by motor 185 forces outer ring 140 to rotate together with disk 145 and scan the patient even though flaps 160 are rubbing against friction lining 115. Optionally, scanning may be performed over 360° (the entire circumference of imaging capsule 100) for a pre-selected amount of time or a pre-selected number of rotations.

In an exemplary embodiment of the invention, when motor 185 is turned off, spring 190 exerts torque on disk 145 causing it to rotate in the opposite direction (e.g. counter clockwise) and to return to the rest position relative to outer ring 140 blocking the emission of radiation.

In some embodiments of the invention, limiters 170 may be placed in various positions to initiate or prevent motion from various positions as explained above and not necessarily in the positions shown in the attached figures.

In an exemplary embodiment of the invention, motor 185 is coupled to a clutch 187 for delivering rotational motion to disk 145. Optionally, clutch 187 allows disk 145 to move freely in the opposite direction when motor 185 is turned off so that the entire motor assembly does not need to rotate in the reverse direction under the torque of spring 190. Optionally, the clutch may be controlled electrically or mechanically to allow free motion in one state and motor controlled motion in the other state.

In some embodiments of the invention, other mechanisms instead of flaps 160 may be used for causing friction between outer ring 140 and encasement 105. Additionally, the roles of disk 145 and outer ring 140 may be reversed so that the motor will drive outer ring 140 and disk 145 will be held by friction with a non moving part of imaging capsule 100.

Figure 5:
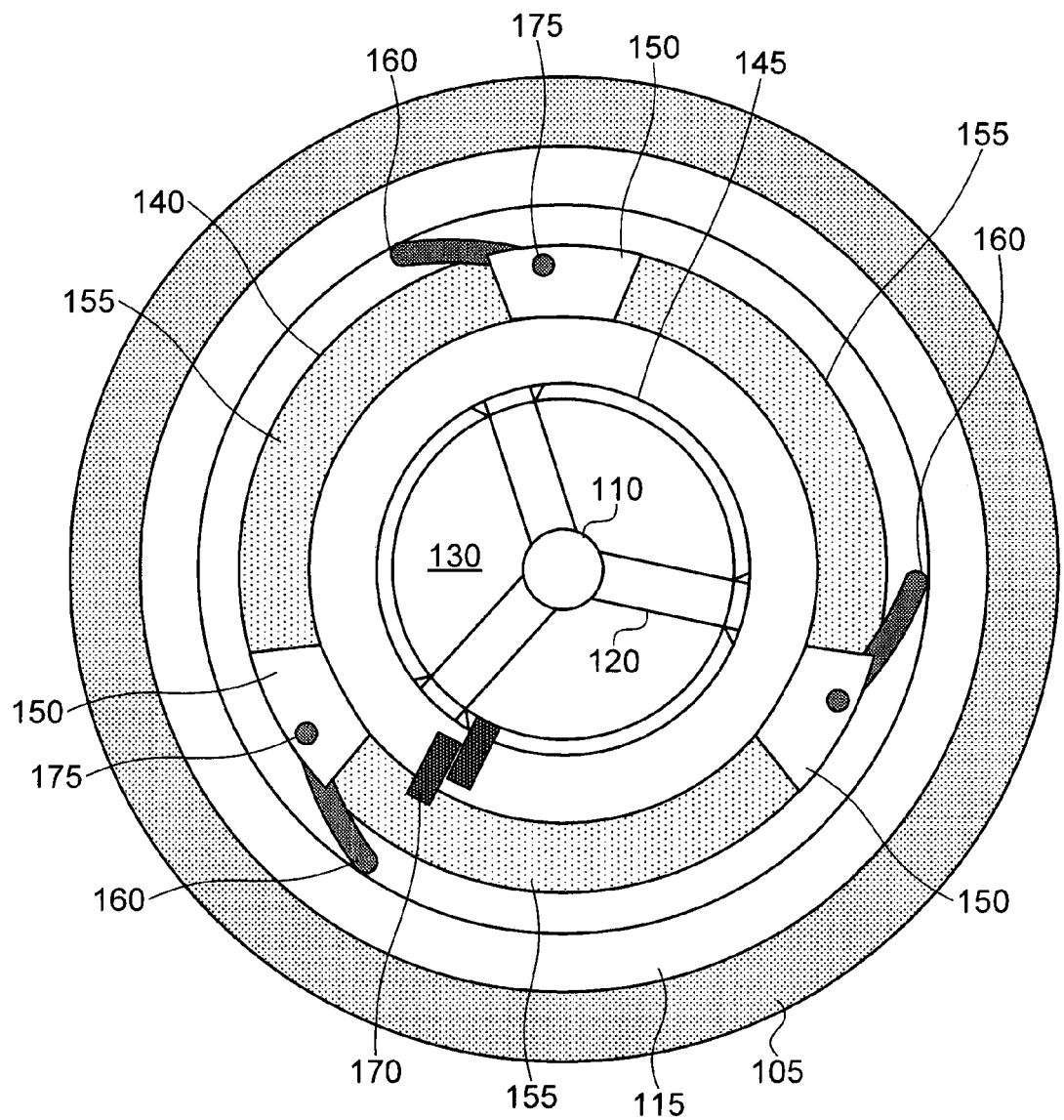
FIG. 5 is a schematic illustration of a top view of a radiation control mechanism in a rotated position without a spring, according to an exemplary embodiment of the invention.

FIG. 5 is a schematic illustration of a top view of a radiation control mechanism 200 in a rotated position without a spring, according to an exemplary embodiment of the invention. In some embodiments of the invention, disk 45 and outer ring 140 are not connected with a spring 190 as described above. Accordingly, power is required to turn the motor and unblock the outlets of collimators 120 as described above. However the outlets are not automatically closed when the motor stops turning because of spring 190. Instead motor 185 is required to change the direction of rotation to restore disk 145 to the rest position relative to outer ring 140 so that the outlets of collimators 120 are blocked by shutters 150.

In an exemplary embodiment of the invention, the friction between flaps 160 and lining 115 is controllable. Optionally, when motor 185 stops turning instead of releasing motor 185 and allowing disk 145 to rotate back to its rest position under the influence of the torque of spring 190, the friction between flaps 160 and lining 115 is canceled and outer ring 140 moves under the influence of the torque of spring 190, so that spring 190 unwinds and disk 145 returns to the rest position relative to outer ring 140 while disk 145 remains stationary.

In an exemplary embodiment of the invention, the friction between flaps 160 and lining 115 is released by instructing hinge 175 to relax its hold on flaps 160 allowing them to move closer to outer ring 140 and thus releasing the friction between them and lining 115. Alternatively, lining 115 may include an electromagnet that is turned on when motor 185 starts turning. The electromagnet exerts a force on flaps 160 inhibiting motion of outer ring 140. Optionally, when motor 185 stops the flaps are released and the torque of spring 190 causes outer ring 140 to rotate such that disk 145 will return to the rest position relative to outer ring 140 thus blocking the emission of radiation.

In some embodiments of the invention, the electromagnetic force acts directly on outer ring 140 and does not require the use of flaps 160. When the electromagnetic force is activated the outer ring will be subject to a friction force that inhibits motion of outer ring 140.

In some embodiments of the invention, lining 115 may be made from a material that expands or contracts causing the flaps to rub against the lining or be released, for example the lining may be a Nitonol spring or wire that changes shape when current passes through it causing it to heat up and expand or contract. Optionally, a Nitinol alloy may have 2 positions: one when current passes through it and friction is required and the other when no current passes through it.

In some embodiments of the invention, lining 115 may include a piezoelectric device that changes size responsive to an electric voltage being applied to it. Optionally, the piezoelectric device can form contact with flaps 160 or outer ring 140 to inhibit motion or the piezoelectric device can release them.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

We claim:

1. An imaging capsule for scanning inside a living body, with a fail-safe radiation mechanism, comprising:
   an encasement for holding and protecting elements forming the imaging capsule; wherein the encasement and elements are configured to be swallowed by a user and flow through a gastrointestinal tract of the user without damaging the elements;
   the elements comprising:
   a power source;
   a radiation source comprising a radioisotope that emits Xrays and/or gamma rays;
   a rotatable disk with the radiation source mounted on the rotatable disk and wherein the rotatable disk has a collimator structure allowing the emission of radiation from the radiation source from one or more locations on the circumference of the rotatable disk;
   an outer ring surrounding the circumference of the rotatable disk and configured to rotate relative to the rotatable disk; the outer ring includes areas with a material that blocks radiation and areas with a material that does not block radiation; wherein the areas that block radiation on the outer ring are positioned so that there exists a rest position of the outer ring relative to the rotatable disk in which the areas that block radiation on the outer ring coincide with the one or more locations on the circumference of the rotatable disk that do not block the emission of radiation;
   a motor powered by the power source for rotating the rotatable disk relative to the outer ring; wherein the rotatable disk and outer ring are initially in the rest position blocking the emission of radiation until the motor is activated to rotate the rotatable disk and allow the emission of radiation; and
   a spring coupling the rotatable disk to the outer ring, wherein the spring is configured to automatically return the rotatable disk and the outer ring to the rest position when the motor is deactivated, thus providing a fail-safe radiation mechanism.

2. An imaging capsule according to claim 1, further comprising flaps extending from the outer ring and an encasement with an inner lining enclosing the imaging capsule, wherein the flaps are in contact with the inner lining of the encasement and are held by a force that prevents the outer ring from rotating responsive to the torque of the spring and the rotation of the rotatable disk.

3. An imaging capsule according to claim 2, wherein the force between the flaps and the inner lining is a friction force.

4. An imaging capsule according to claim 2, wherein the force between the flaps and the inner lining is an electromagnetic force.

5. An imaging capsule according to claim 2, wherein the force between the flaps and the inner lining is controllable.

6. An imaging capsule according to claim 5, wherein if the motor is deactivated and the force between the flaps and the inner lining is turned off, the outer ring will rotate to return the rotatable disk and outer ring to the rest position.

7. An imaging capsule according to claim 5, wherein if the motor is deactivated and the force between the flaps and the inner lining is turned on, the rotatable disk will rotate to return the rotatable disk and outer ring to the rest position.

8. An imaging capsule according to claim 7, wherein the motor is connected to the rotatable disk with a clutch that allows the motor to rotate the rotatable disk in a specific direction and the rotatable disk can rotate back freely when the motor is deactivated.

9. An imaging capsule according to claim 1, wherein the encasement has an inner lining, which includes an electromagnet that applies an electromagnetic force on the outer ring, wherein the electromagnet controllably prevents the outer ring from rotating responsive to the torque of the spring and the rotation of the rotatable disk.

10. An imaging capsule according to claim 1, further comprising a first limiter attached to the rotatable disk and a second limiter attached to the outer ring, wherein the limiters prevent the rotatable disk and outer ring from leaving the rest position under the influence of the spring and the limiters force the outer ring to rotate with the rotatable disk under the force of the motor.

11. An imaging capsule according to claim 1, wherein the rotatable disk and the outer ring are configured to controllably emit radiation 360 degrees around the rotatable disk.

12. An imaging capsule according to claim 1, wherein the rotatable disk and the outer ring are configured to controllably emit radiation for a pre-selected amount of time or a pre-selected number of rotations.

13. An imaging capsule according to claim 1, further comprising a transceiver to receive instructions to activate or deactivate the motor.

14. An imaging capsule according to claim 1, wherein the imaging capsule is pre-programmed to activate or deactivate the motor at specific times.

15. A method of providing fail-safe radiation while scanning inside a living body, comprising:
   enclosing elements in an encasement to form an image capsule with protected elements; wherein the encasement and elements are configured to be swallowed by a user and flow through a gastrointestinal tract of the user without damaging the elements;
   assembling the elements of the imaging capsule comprising:
   mounting a radiation source comprising a radioisotope that emits Xrays and/or gamma rays on a rotatable disk;
   positioning collimators on the rotatable disk so that the radiation is allowed to be emitted from one or more locations on the circumference of the rotatable disk;
   placing an outer ring to surround the circumference of the rotatable disk and configured to rotate relative to the rotatable disk; wherein the outer ring includes areas with a material that blocks radiation and areas with a material that does not block the emission of radiation;

situating the outer ring and rotatable disk initially in a rest position in which the location of the areas that block radiation on the outer ring coincide with the one or more locations on the circumference of the rotatable disk that do not block the emission of radiation;

receiving instructions to begin emitting radiation; and activating a motor powered by a power source in the encasement to rotate the rotatable disk relative to the outer ring to a position that allows the emission of radiation;

connecting between the rotatable disk and the outer ring with a spring so that they will return to the rest position automatically when the motor is deactivated, thus providing a fail-safe radiation mechanism.

16. An imaging capsule according to claim 9, further comprising a first limiter attached to the rotatable disk and a second limiter attached to the outer ring, wherein the limiters prevent the rotatable disk and outer ring from leaving the rest position under the influence of the spring and the limiters force the outer ring to rotate with the rotatable disk under the force of the motor.

17. An imaging capsule according to claim 1, further comprising one or more detectors that detect backscattered particles resulting from the emission of radiation by the radiation source.

18. A method according to claim 15, further comprising detecting backscattered particles resulting from the emission of radiation by the radiation source with one or more detectors in the imaging capsule.

19. A method according to claim 15, wherein the encasement has an inner lining, which includes an electromagnet that applies an electromagnetic force on the outer ring, and wherein the electromagnet controllably prevents the outer ring from rotating responsive to the torque of the spring and the rotation of the rotatable disk.

* * * * *